US00PP18322P3

(12) United States Plant Patent
Stansberry

(10) Patent No.: US PP18,322 P3
(45) Date of Patent: Dec. 18, 2007

(54) ***ARGYRANTHEMUM* PLANT NAMED STANS001**

(50) Latin Name: *Argyranthemum frutescens*
Varietal Denomination: Stans001

(75) Inventor: Sylvia R. Stansberry, Gibbon, NE (US)

(73) Assignee: Amerinova Properties, LLC, Bonsall, CA (US)

( * ) Notice: Subject to any disclaimer, the term of this patent is extended or adjusted under 35 U.S.C. 154(b) by 0 days.

(21) Appl. No.: 11/333,010

(22) Filed: Jan. 17, 2006

(65) Prior Publication Data

US 2007/0169240 P1 Jul. 19, 2007

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para

(57) ABSTRACT

A new and distinct cultivar of *Argyranthemum* plant named Stans 001, particularly characterized by its deep lavender mature ray florets which have a white area near the base so as to form a white ring around the central yellow disk, full and tight growth with compact habit, excellent branching, and its floriferous habit.

1 Drawing Sheet

The present invention relates to a new and distinct cultivar of *Argyranthemum* plant, botanically known as *Argyranthemum frutescens,* and referred to by the variety denomination Stans001.

The new cultivar was discovered by the inventor in March 2001 as a seedling growing among other seedling plants of the species *Argyranthemum frutescens* in a greenhouse in Hobbs, N. Mex. Both the male and female parents are unknown. The new cultivar was recognized by its interesting white to lilac colored flower petals when the flowers first open and which transition to a deeper lilac purple when fully open. The inner ends of the petals are white which together form a white ring around a vibrant yellow eye.

The first act of asexual reproduction of the new cultivar was accomplished when vegetative cuttings were taken in spring 2002 in a controlled environment in Hobbs, N. Mex., by or under the supervision of the inventor. Horticultural examination of controlled flowerings of successive plantings has shown that the unique combination of characteristics of the new cultivar are firmly fixed and are retained through successive generations of asexual reproduction.

The new cultivar has not been observed under all possible environmental conditions. The phenotype may vary significantly with variations in environment, such as temperature, light intensity, and daylength without, however, any variance in genotype. The following observations, measurements, and comparisons describe plants approximately nine weeks old grown in Bonsall, Calif., under normal commercial growing conditions.

SUMMARY OF THE INVENTION

The following traits have been repeatedly observed and have been determined to be basic characteristics of the new cultivar, which, in combination, distinguish the new cultivar as being new and distinct:

1. The immature ray florets are white to light lavender, with mature ray florets being a distinct lilac purple in color, with a small area of white at the base. When the entire flower is viewed from above, the white areas at the base of all the ray florets form a distinctive white ring around the central disc.
2. Well-branched.
3. Full and tight growth, with compact habit.
4. Floriferous habit.
5. The flowers are medium to large in size, ranging from 4 cm to slightly greater.

The most similar cultivars to which 'Stans001' can be compared are Maderia TM Pink and the patented cultivar 'Cobsing', disclosed in U.S. Plant Pat. No. 13,541. Compared to 'Cobsing', 'Stans001' has a similar habit but has a much more intense pink flower color, with darker shading toward the center. 'Cobsing' has a pale flat pink flower color. Compared to Maderia TM Pink, both cultivars are similar in height and growth habit, but Maderia TM Pink has larger flowers which are a deeper shade of pink, and a center with a deep rust hue outlined by yellow.

BRIEF DESCRIPTION OF THE PHOTOGRAPHIC DRAWING

The photograph at the bottom of the sheet shows a front perspective view of a typical flowering plant of the new cultivar. The photo at the top of the sheet comprises a close-up view showing buds, flowers just opening and fully open, and leaves. The colors in the photographs are as true as is reasonably possible to obtain with colored reproductions of this type. A few of the just fully opened flowers in the lower photo show the true vivid purple ray floret color of the new cultivar, while other flowers shown in both photos depict the ray floret color as being somewhat lighter. The color values stated below in the detailed description are accurate. The photos were taken at approximately 11 a.m. under bright filtered natural light.

DETAILED BOTANICAL DESCRIPTION

In the following description, color references are made to The Royal Horticultural Society Colour Chart. The values are based on plant material grown in Bonsall, Calif.

Botanical classification: *Argyranthemum frutescens* cv Stans001.

Parentage:

*Seed parent.*—Unknown.

*Pollen parent.*—Unknown.

Propagation:

*Type.*—By leaf cuttings.

*Time and temperature to initiate roots.*—Approximately 7 to 10 days at 20 degrees Centigrade. A rooted cutting is produced in approximately 28 to 32 days at 20 degrees Centigrade.

*Rooting description.*—Fibrous, moderately thick, white in color.

*Rooting habit.*—Very dense, freely branching.

Plant description:

*Habit.*—Stans 001 is a round, very upright but compact plant with a V-shaped profile. The habit is very uniform. Plant height is 42 cm. with a diameter of 57 cm. It is a perennial in mild winters (hardy to 30 degrees Fahrenheit), and has excellent vigor and very free-branching. Pinching is recommended for best branching. No basal shoots were observed.

*Lateral shoots.*—The number of lateral shoots varies, but averages nine per plant. Lateral branch length is also variable, but averages approximately 34 cm. with a 0.6 cm. diameter. Internode length is 1.0 cm., and main stems have several secondary shoots.

*Stems.*—Stems are upright to somewhat outwardly inclined due to the secondary laterals. Stem color is 147C, speckled with 182A. No pubescence. Stems are very strong, tough and somewhat woody at base. Very dense foliage.

*Leaves.*—Leaves are alternate, simple, but deeply dissected with narrow blades and deep sinuses. The leaves have five to seven narrow lobes projecting from a 0.3 cm. wide center blade. Leaf tips are acute, and leaf bases are attenuate. Leaf margins are entire, but lobed with deep, parallel sinuses. Leaf length averages 4.2 cm. and the entire width of the leaf is 3.0 cm. Leaf texture is smooth, venation pattern is pinnate, and there is no pubescence.

Young leaves are 146A top side and 146B lower side. Mature leaves are 147A top and 147B bottom. Upper side vein color is 147A and lower side vein color is 147B.

Petioles are 1.5 cm. long and 0.2 cm. wide. Petioles are smooth on both sides, and both sides are 147B in color. Foliage is very durable, with the tough, narrow blades being well adapted for drought. The leaves form a uniform, dense canopy with the flowers being held well above the foliage. No stipules, tendrils, thorns, or spines were observed.

*Flowers.*—Inflorescence arrangement is solitary and both terminal and axillary, producing actinomorphic, medium-size daisies. The plant is very floriferous. Each primary stem has approximately 14 inflorescences and approximately 22 buds. Plants have greater than 350 inflorescences, and flowering continues on new lateral growth.

Inflorescences open in five to seven days and have a faint sour odor. They are upright or curving outwardly and upwardly on lateral shoots. The round flowers are 4.0 cm. or slightly greater in diameter and 1.5 cm. in height. Disk diameter is 1.4 cm. Receptacles are shallow and bowl-like, 1.4 cm. in diameter and 0.7 cm. in height. Inflorescence longevity varies with temperatures, but average seven to ten days.

Bud length just before anthesis is 1.2 cm. and diameter is 0.8 cm. Buds are oval in shape, and bud color is 155D. Buds open in four to five days.

There is only one whorl of 20 rays florets. Ray florets are smooth to shallowly ridged, are nearly horizontal in aspect, and encircle a compact disk. Ray florets are ligulate, approximately 1.8 cm. long and 0.5 cm. wide. Apices are minutely tridentate, bases are acute.

Ray floret color when opening is 155D on both top and bottom sides. As the florets open, the floret color becomes lavender and then a deeper lavender or lilac color (77B) when fully open and mature. When fully mature, there is a small area of 155D at the base. This results in a white ring around the central disk when viewed from above, giving sort of a bull's-eye effect, particularly with the rusty red tips of immature disk florets. Lower surfaces of ray florets are 75C with 155D at bases. Color fades to 77C and, in extreme heat, to nearly white (155D).

There are 188 disk florets in a round, compact, mounding center. Disk florets are tiny, five-pointed, and tubular. Apices are acute, and the bases are fused into a tube. Disk florets are 0.6 cm. long, apices are 0.2 cm. wide, and bases are less than 0.1 cm. wide.

Immature disk florets are 178A, a rusty red-brown that appears as a darker center "eye" that eventually disappears as all the florets open. After anthesis, disk florets are 12A at apices, 12D at midsection, and 157A at bases. No receptacle spines were observed.

Involucre bracts of the inflorescence are imbricate, overlapping to form a shallow bowl. There are approximately 23 elliptical bracts, with both the top and bottom surfaces being smooth. They are 0.3 cm. long and 0.2 cm. wide. Involucre bract color is 145A above and 147B below.

Each shoot tip has three daisies. The terminal peduncle is 11.5 cm., the secondary axillary peduncle is 15.3 cm., and the third axillary peduncle is 12.0 cm. long. Peduncles are 0.15 cm. in diameter — very upright if terminal — and at a 45 degree angle from the stem axis if axillary. Peduncle strength is very good, and the peduncles are smooth to slightly ridged. Peduncle color is 146B. No pubescence.

*Reproductive organs.*—Disk florets have five stamens with tiny (less than 0.1 cm.) oval anthers which are 13B in color. Pollen is very scarce, and is also 13B when present.

There is one pistil per each ray and disk floret, although disk floret pistils are very much reduced and are probably nonfunctional. For the ray florets, the pistils are 0.7 cm. long. Stigmas are bipartite, and 13A in color. Style length is 0.4 cm.,and style color is 157C. Ovary color is 157A.

Disease and insect resistance: To date, the new cultivar has been observed to have normal resistance to plant disease and insects.

I claim:

1. A new and distinct cultivar of *Argyranthemum* plant named Stans 001, as illustrated and described.

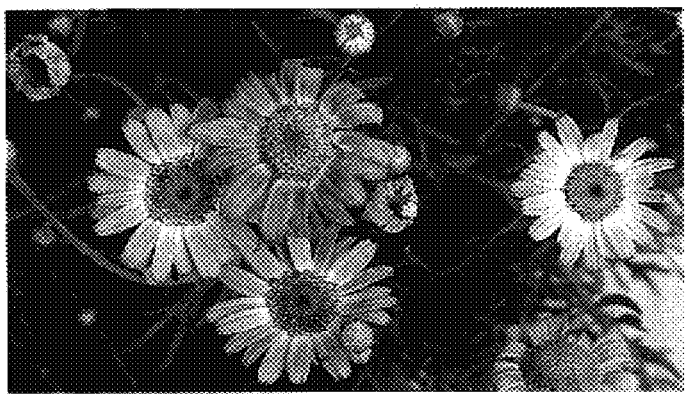
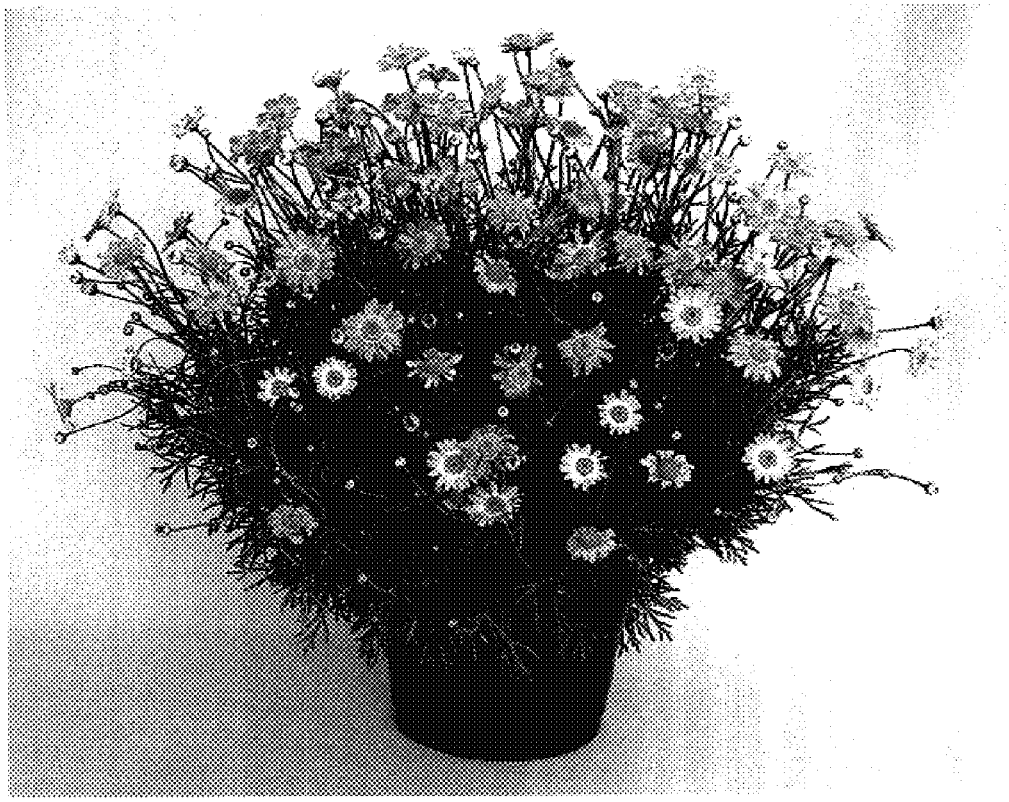

* * * * *